(12) United States Patent
Olalde Rangel

(10) Patent No.: US 7,658,956 B2
(45) Date of Patent: Feb. 9, 2010

(54) ERECTILE DYSFUNCTION PHYTO-NUTRACEUTICAL SYNERGISTIC COMPOSITION

(75) Inventor: Jose Angel Olalde Rangel, 519 Cleveland St., Suite 101, Clearwater, FL (US) 33755

(73) Assignee: Jose Angel Olalde Rangel

( * ) Notice: Subject to any disclaimer, the term of this patent is extended or adjusted under 35 U.S.C. 154(b) by 346 days.

(21) Appl. No.: 11/460,674

(22) Filed: Jul. 28, 2006

(65) Prior Publication Data

US 2008/0026082 A1   Jan. 31, 2008

(51) Int. Cl.
*A61K 36/00* (2006.01)
*A61K 36/25* (2006.01)
*A61K 36/254* (2006.01)
*A61K 36/074* (2006.01)
*A61K 36/28* (2006.01)

(52) U.S. Cl. .................. 424/725; 424/728; 424/195.15; 424/737; 424/767

(58) Field of Classification Search .................. 424/439, 424/725, 728, 195.15, 737, 767
See application file for complete search history.

(56) References Cited

U.S. PATENT DOCUMENTS 4,804,672 A * 2/1989 Yamaguchi et al. ......... 514/392

* cited by examiner

*Primary Examiner*—Alton N Pryor

(57) ABSTRACT

A Phytoceutical composition for the prevention and treatment of erectile dysfunction is provided. A specific combination of extracts of plants and nutraceuticals is based on categorizing plants and nutraceuticals into one of three groups, Energy, Bio-Intelligence, and Organization. Such combination has synergistic effects, with minimal side effects.

2 Claims, 1 Drawing Sheet

Figure 1: Plants and nutraceuticals are classified under Energy, Intelligence and Organization principles; also, in accordance to classification in Table 1.
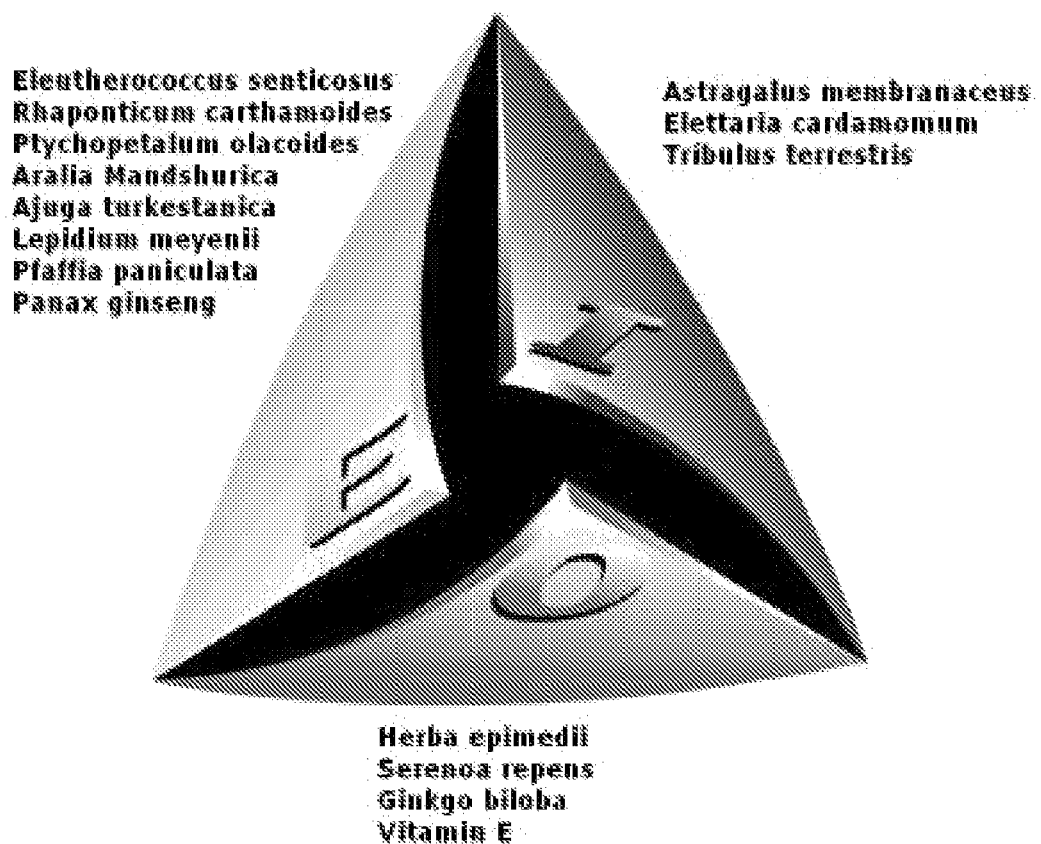

ERECTILE DYSFUNCTION PHYTO-NUTRACEUTICAL SYNERGISTIC COMPOSITION

PRIOR RELATED APPLICATIONS

Not applicable.

FEDERALLY SPONSORED RESEARCH STATEMENT

Not applicable.

REFERENCE TO MICROFICHE APPENDIX

Not applicable.

FIELD OF THE INVENTION

The invention relates to a phytoceutical formulation used to treat erectile dysfunction disorders. The formulation is a particular combination of plants that have synergistic effect in combination. Principles for selecting beneficial formulations are provided.

BACKGROUND OF THE INVENTION

The academic study of medicinal plants for the treatment of diverse diseases has been nearly as pervasive as the study of Western medicines. The active principles from many traditional medicines have been extracted from plants, the curative agents identified and their mechanisms of action determined. Plant based medicines are typically well tolerated, with less severe side effects as well as a smaller range of side effects. In contrast, while synthetic drugs can be highly effective, their use is often hampered by severe side effects. Additionally, while synthetic pharmaceuticals are based upon single chemicals, many phytomedicines exert their beneficial effects through the additive or synergistic action of several chemical compounds acting at single or multiple target sites associated with a physiological process. As pointed out by Tyler (1999), this synergistic or additive pharmacological effect can be beneficial by eliminating the problematic side effects associated with the predominance of a single xenobiotic compound in the body. In this respect, Kaufman et al. (1999) extensively documented how synergistic interactions underlie the effectiveness of a number of phytomedicines. This theme of multiple chemicals acting in an additive or synergistic manner likely has its origin in the functional role of secondary products in promoting plant survival. For example, in the role of secondary products as defense chemicals, a mixture of chemicals having additive or synergistic effects at multiple target sites would not only ensure effectiveness against a wide range of herbivores or pathogens but would also decrease the chances of these organisms developing resistance or adaptive responses (Kaufman et al., 1999; Wink, 1999). Conclusion: On one hand, synthetics may have the required efficacy for disease treatment; however this can be marred by severe side effects. On the other hand, despite the excellent medicinal qualities of many plants, they are individually insufficient to take chronic degenerative diseases into remission. However, there is mounting evidence which demonstrates that medical plants contain synergistic efficacy and/or side-effect neutralizing combinations (Gilani and Rahman, 2005). Thus, what are needed in the art are better treatment regimes with improved patient tolerance, while providing sufficient efficacy.

SUMMARY OF THE INVENTION

A number of known beneficial plants and tonics were classified according to their capacity to enhance the three main elements that support overall health: Energy (E), Bio-intelligence (I) and Organization (O). A synergistic effect is expected when all three categories of herbs (E, I, O) are included in a formulation, preferably at least two or three or four plants from each category. Thus, one embodiment of the invention provides the selection of disease treating formulations according to these principles. An example of a formulation prepared this way is provided and additional formulations are being prepared and tested.

Another embodiment of the invention provides an effective, natural composition for treating erectile dysfunction disorders and symptoms. The composition can be used alone, or can be combined with simultaneous use of one or more pharmaceutical compositions.

BRIEF DESCRIPTION OF THE DRAWING

FIG. 1: Plants and nutraceuticals are classified under Energy, Intelligence and Organization principles.

DETAILED DESCRIPTION OF THE INVENTION

"Pharmaceutically acceptable excipients" is used herein according to art accepted meanings, and includes those ingredients needed to formulate a medicine for mammalian use, including the use of gelatin capsules.

"Synergistic" or "synergy" is used herein to mean that the effect is more than its additive property. In preferred embodiments, the synergy is at least 1.5, 2, 5, or 10 fold.

By use of "plants," what is meant herein is that the plant (or that portion with medicinal activity) is used whole, ground, or as an extract. Also included are purified active ingredients and derivatives thereof. However, it is believed that the best efficacy of plants used herein is achieved with the use of the entire plant or its extracts, rather than with the use of isolated active ingredients.

Further, although plants are named here according to commonly used nomenclature, with improving taxonomy plants are often reclassified. Whenever a plant is referenced, it includes related species with similar active ingredients.

The following examples are illustrative only and should not serve to unduly limit the invention.

Example 1

Plant Characteristics—Erectile Dysfunction

Energy Enhancing Phytoceuticals

*Ajuga turkestanica*: Its main active principle turkesterone, a phytoecdysteroid possessing an 11alpha-hydroxyl group. Ecdysteroids normalize NADH dehydrogenase activity, enzyme which catalyzes electron transfer from NADH to ubiquinones in the oxidative phosphorylation processes which occur at the mitochondrial level, contributing to the potential electrochemical buildup required to produce ATP. It also normalizes the succinate dehydrogenase enzyme which participates in the tricarboxilic acid cycle, which translates to ATP synthesis and patient energy level increases [Tashmukhamedova M A, Almatov K T, Syrov V N. Comparative study of the effect of ecdysterone, turkesterone and nerobol on the function of rat liver mitochondria in experimental diabetes. *Vopr Med Khim.* 1986; 32:24-8].

*Aralia mandshurica* (Manchurian Thorn Tree) The main active principles are triterpene saponins aralosides (elatosides). Siberians traditionally preferred *Aralia* for immune health, to reduce stress/depression, and to improve physical and mental performance. Siberians would often combine *Aralia* with other adaptogens for maximal stress reduction/performance enhancement benefits. *Aralia* extract was included in the official Russian Pharmacopoeia in 1983 as a treatment for the symptoms of stress overload, such as fatigue, weakness, headache, libido loss, depression, immune weakness, etc. G. P. Gubina reported in 1988 a 90 percent success rate—using *Aralia*—in 106 patients treated for various "asthenic" (stress overload/weakness) conditions. *Aralia* enhances a person's ability for memorization and prolonged concentration. In proofreading tests, after taking this plant, a decrease in the quantity of mistakes was observed in 88 percent of the experimental group, while an increase in the quantity of mistakes was observed in 54 percent of the control group. Those taking *Aralia mandshurica* exerted a strong stimulating influence among test subjects who displayed a great improvement in reading comprehension, aptitude and speed. [A. A. Lebedev/Far East Scientific Center of the USSR]; [V. V. Kazakevich/Academy of Sciences, Vladivostok, Russia].

*Eleutherococcus* or *Acanthopanax senticosus* (Russian Ginseng, Siberian Ginseng, *Eleutherococcus*, Devil's Shrub, Touch-me-not, No me toques, Wild Pepper, Shigoka, Acantopanacis senticosus, Buisson du diable, chi wu cha, ciwujia, eleutherococc, eleutherococoque, eleutherokokk koljucij, ezoukogi, gashi ohgap, hongmao-wujiapi, pai wu cha pi, shigoka, Stachelkraftwurz, Stachelpanax, Taigawurzel, tsu wu cha, wu cha sang, wu cha seng, wu jia pi) Contains terpenoids (oleanolic acid), Eleutheroside A (daucosterol), Eleutheroside B (siringin), Eleutheroside B1 (isofraxidin), Eleutheroside B4 (sesamin); Eleutheroside D and E (heteroside siringoresinol); Eleutheroside C, G, I, K, L and M; phytosterols (β-sitosterol), polysaccharides (eleutherans), volatile oils, caffeic acid, coniferyl aldehyde, and sugars. One study demonstrated the vasodilating effects of *Eleutherococcus*. The vascular effect is endothelium-dependent and mediated by NO and/or EDHF depending on the vessel size. Other vasorelaxation pathways, such as inhibition of K(+)-channels and activation of muscarinic receptors, may also be involved (Kwan CY, Zhang W B, Sim S M. Vascular effects of Siberian ginseng (*Eleutherococcus senticosus*): endothelium-dependent NO- and EDHF-mediated relaxation depending on vessel size. Naunyn Schmiedebergs Arch Pharmacol. 2004; 369: 473-80). *Eleutherococcus senticosus* has been suggested to improve cardio respiratory fitness (CF) and fat metabolism (FAM), therefore, endurance performance (EP). Studies that evaluated the effects of ES during endurance exercise, suggest that Eleuthero substantially improves CF, FAM, and EP. (Goulet E D, Dionne I J. Assessment of the effects of *eleutherococcus senticosus* on endurance performance. Int J Sport Nutr Exerc Metab. 2005; 15:75-83). Eleuthero has anti-platelet aggregation activity similar to aspirin (this may improve microvascular circulation); it also has antioxidant activity. Russian Ginseng contains at least 40 active ingredients.

*Lepidium meyenii* (Maca, maca-maca, maino, ayak chichira, and ayak willku) Its main active principles are alkaloids (Macaridine, Lepidiline A and B); bencil-isotiocyanate and glucosinolates; macamides, beta-ecdysone and fitosterols. These substances activate ATP synthesis which confers energizing properties. They also diminish variations in homeostasis produced by stress because they reduce corticosterone's high levels; prevent glucose diminution and the increase of suprarenal glands' weight due to stress. They also restore homeostasis and improve energy (Lopez-Fando A, Gomez-Serranillos M P, Iglesias I. *Lepidium peruvianum* chacon restores homeostasis impaired by restraint stress. Phytother Res. 2004; 18:471-4). A double blind placebo-controlled, randomized, parallel trial study in which active treatment with different doses of *Lepidium meyenii* was compared with placebo showed an improvement in sexual desire. (Gonzales G F, Cordova A, Vega K. Effect of *Lepidium meyenii* (MACA) on sexual desire and its absent relationship with serum testosterone levels in adult healthy men. Andrologia. 2002; 34:367-72). *Lepidium meyenii* also improves sperm production and sperm motility by mechanisms not related to LH, FSH, PRL, T and E2 (Gonzales G F, Cordova A, Gonzales C. *Lepidium meyenii* (Maca) improved semen parameters in adult men. Asian J Androl. 2001; 3:301-3).

*Panax ginseng* (Chinese ginseng, panax, ren shen, jintsam, ninjin, Asiatic ginseng, Japanese ginseng, Oriental ginseng, Korean red ginseng) The main active components are ginsenosides (protopanaxadiols and protopanaxatriols types) these have been shown to have a variety of beneficial effects, including anti-inflammatory, antioxidant, and pro-erectile activity. They also confer energizing properties because they increase ATP synthesis. Studies indicate that *Panax* improves physical and mental performance; and increases resistance to exogenous stress factors.

Korean red ginseng (*Panax ginseng*) is a safe, widely available alternative remedy that improves patients' ability to achieve and maintain an erection sufficient for intercourse, even in a population with severe erectile dysfunction. It is a reasonable, nonprescription treatment, especially for men with reservations about taking sildenafil (Price A, Gazewood J. Korean red ginseng effective for treatment of erectile dysfunction. J Fam Pract. 2003; 52:20-1). A clinical, randomized, controlled trial showed that Korean ginseng can be as effective alternative for treating male erectile dysfunction. 45 patients with clinically diagnosed erectile dysfunction were enrolled in a double-blind, placebo controlled, crossover study in which the effects of Korean ginseng and a placebo were compared. Mean International Index of Erectile Function scores were significantly higher in patients treated with Korean red ginseng than in those who received placebo. Scores on questions (penetration and maintenance) were significantly higher in the ginseng than in the placebo group. In response to the global efficacy question 60% of the patients answered that Korean red ginseng improved erection. Among other variables penile tip rigidity on RigiScan showed significant improvement for ginseng versus placebo (Hong B, Ji Y H, Hong J H. A double-blind crossover study evaluating the efficacy of korean red ginseng in patients with erectile dysfunction: a preliminary report. J Urol. 2002; 168:2070-3). Another study confirmed that the long-term administration of Korean ginseng enhances erectile capacity and that its action is mediated by endothelium-derived relaxing factor and peripheral neurophysiologic enhancement (Choi Y D, Rha K H, Choi H K. In vitro and in vivo experimental effect of Korean red ginseng on erection. J Urol. 1999; 162:1508-11). The effects of ginseng treatments were compared to placebo and other drug. A total of 90 patients with 30 patients in each group were closely followed. In the group receiving ginseng, changes in early detumescence and erectile parameters such as penile rigidity and girth, libido and patient satisfactions were significantly higher than that of other groups. The overall therapeutic efficacies on erectile dysfunction were 60% for ginseng group and 30% for placebo and trazodone treated groups, statistically confirming the effect of ginseng. If administered for a prolonged period of time, the cumulative effect on vascular flow might be seen (Choi H K, Seong D H, Rha K H. Clinical efficacy of Korean red ginseng for erectile dysfunction. Int J Impot Res. 1995; 7:181-6). Recent studies in laboratory animals have shown that both Asian and American forms of ginseng enhance libido and copulatory performance.

These effects of ginseng are due to direct effects of ginseng, or its ginsenoside components, on the central nervous system and gonadal tissues. Indeed, there is good evidence that ginsenosides can facilitate penile erection by directly inducing the vasodilatation and relaxation of penile corpus cavernosum. Moreover, the effects of ginseng on the corpus cavernosum appear to be mediated by the release and/or modification of release of nitric oxide from endothelial cells and perivascular nerves. The incorporation of this phytomedicine provides at least 86 active principles in a single therapeutic.

*Pfaffia paniculata* (Suma, Brazilian Ginseng, Pfaffia, Para Tudo, Corango-acu; also *Hebanthe paniculata, Gomphrena paniculata, G. eriantha, Iresine erianthos, I. paniculata, I. tenuis, P. eriantha, Xeraea paniculata*) contains active glycosides (beta-ecdysone and three ecdysteroids), six different pfaffic acids, phytosterols (sitosterol and estigmasterol). Pfaffia also contains saponins and 19 different amino acids, minerals, vitamins and pantoneic acid. Its germanium content probably accounts for its properties as an oxygenator at the cellular level and its high iron content may account for its traditional use for anemia. It's phytosterols are precursors of the synthesis of Testosterone. The incorporation of this phytomedicine provides 44 active principles in a single therapeutic.

*Ptychopetalum olacoides* (muira puama) The main plant chemicals found in muira puama include: alpha-copaene, alpha-elemene, alpha-guaiene, alpha-humulene, alpha-muurolene, alpha-pinene, alpha-resinic acid, alpha-terpinene, arachidic acid, allo-aromadendren, behenic acid, beta-bisabolene, beta-caryophyllene, beta-pinene, beta-resinic acid, beta-sitosterol, beta-transfarnesene, borneol, campesterols, camphene, camphor, car-3-ene, caryophyllene, cerotic acid, chromium, coumarin, cubebene, delta-cadinene, dotriacontanoic acid, elixene, ergosterols, eugenol, essential oils, gamma-muurolene, hentriacontanoic acid, heptacosanoic acid, lignoceric acid, limonene, linalool, lupeol, melissic acid, montanic acid, muirapuamine, myrcene, nonacosanoic acid, para-cymene, pentacosanoic acid, phlobaphene, stigmasterols, trichosanic acid, and uncosanic acid. The benefits of muira puama have been studied in two human trials in France, reporting that it was effective in improving libido and treating erectile dysfunction. One had 262 male patients who experienced lack of sexual desire and the inability to attain or maintain an erection, 62% of the patients with loss of libido reported that the extract of muira puama "had a dynamic effect," and 51% of patients with erectile dysfunction felt that muira puama was beneficial. The second study evaluated positive psychological benefits of muira puama in 100 men with male sexual weakness. The therapeutic dosage was 1.5 g of a muira puama extract daily. In their final report, researchers indicated muira puama could "enhance libido [in 85% of test group], increase the frequency of intercourse [in 100%] and improve the ability to maintain an erection [in 90%]." In other recent clinical research, muira puama extracts have been reported to have adaptogenic, antifatigue, antistress, and beneficial effects on the central nervous system. A specially-prepared extract from the root of muira puama has been patented for its ability to "relieve physical and mental fatigue" and for "ameliorating a weakened constitution." The root was found to inhibit stress-induced ulcers, while the leaf demonstrated an analgesic effect. Another U.S. patent has been filed on muira puama, citing that it can "reduce body fat percentage, increase lean muscle mass and lower cholesterol" in humans and animals with long-term use (and with no toxicity noted). The newest research confirms muira puama's traditional use for memory and nervous disorders. Toxicity studies with mice indicate no toxic effects. Dr. James Duke, Head of the Medical Plants Laboratory at the American Department of Agriculture, among other renowned experts, recommend this plant for the treatment of erectile dysfunction and decrease in libido.

*Rhaponticum carthamoides* (Leuzea carthamoides, or Maral Root) contains a mixture of compounds called 'levseins'. Levseins represents a complex of more than 10 ecdysterones including 20-beta-ecdysterone, makisterone C, 24-dehydromakisterone A, carthamosterone, polypodyne B and ajugasterone C. Researchers extracted and purified various ecdysteroids from *Rhaponticum* and found that the ecdysteroids increased the muscle mass in a dose-dependent manner, with the rate of increase proportional to the ecdysteroids content. Ecdysteroids normalize NADH dehydrogenase activity, enzyme which catalyzes NADH electron transfer to the ubiquinone in the oxidative phosphorylation processes at the mitochondrial level, contributing to buildup the electrochemical potential used to produce ATP. It also normalizes the succinate dehydrogenase activity, enzyme which acts in the tricarboxilic acid cycle, which translates in ATP synthesis and patient energy level increases [Tashmukhamedova M A, Almatov K T, Syrov V N. Comparative study of the effect of ecdysterone, turkesterone and nerobol on the function of rat liver mitochondria in experimental diabetes. *Vopr Med Khim*. 1986; 32:24-8]. Incorporation of this phytomedicine in a composition provides at least 10 active principles in a single therapeutic.

Bio-Intelligence Modulators.

*Astragalus membranaceus* (Huang-Qi, Huangqi) This plant contains three main types of active principles. Isoflavones, astragalans, and astragalosides which act as modulators of the hypothalamus-hypofisis-adrenal axis response. It also conveys antioxidative properties. Huang-qi, a traditional Chinese medicine, has been used to treat male infertility. 30 infertile male volunteers were studied in vitro. The results showed that percent viability, number of progressive motile spermatozoa, curvilinear velocity, average path velocity and amplitude of lateral head displacement were significantly enhanced by *A. membranaceus*. It is suggested that *A. membranaceus* can enhance the motility of human spermatozoa in vitro (Liu J, Liang P, Yin C. Effects of several Chinese herbal aqueous extracts on human sperm motility in vitro. Andrologia. 2004; 36:78-83). Testis coefficient, testicular sperm count, daily sperm production and epididymal sperm count in the *Astragalus membranaceus* group increased significantly. The percentage of sperm abnormality in the *Astragalus membranaceus* group decreased significantly (Liang P, Li H, Peng X. Effects of *Astragalus membranaceus* injection on sperm abnormality in Cd-induced rats. Zhonghua Nan Ke Xue. 2004; 10:42-5, 48). *Astragalus* membranaceus showed a significant stimulatory effect. It increased the motility of sperm in semen. (Hong C Y, Ku J, Wu P. *Astragalus* membranaceus stimulates human sperm motility in vitro. Am J Chin Med. 1992; 20:289-94). This plant offers at least 38 active principles in a single therapeutic.

*Elettaria cardamomum* (Cardamom) For centuries, Arab cultures have held this spice in high esteem as an aphrodisiac. The medicinal parts are the oil extracted from the seeds and fruit plus seeds. Chief compounds are 1,8-cineol (eucalyptol), alpha-terpinyl acetate, alpha-terpinene, alpha-terpineol, linalyl acetate and fatty oils. Cineol is a central nervous system stimulant with activity. The inclusion of this phytomedicine provides no less than 88 active principles in a single therapeutic.

*Tribulus terrestris* (Puncture Vine, Caltrop, Yellow Vine, bindy eye, bindii, bullhead, burnut, burra gokhroo, caltrop, calthrops, cat's head, common dubbeltjie, devil's thorn, devil's weed, doublegee, dubbeltje, goathead, gokshura, ground bur-nut, isiHoho, land caltrop, Maltese cross, Mexican sandbur, puncture vine, puncture weed, rose, small caltrops, tackweed, Texas sandbur, yellow vine and Goathead).

The fruits and roots of *Tribulus* contain active principles such as: phytosterols, flavonoids, alkaloids, glucosides and steroidal saponins of the furostanol sub-class with a predominant amount of protodioscine (no less than 45%) which seems to be the principle that produces the clinical results in sexuality. These exert an effective stimulant effect over the sexual and reproductive systems, with the increase in body mass, vigour and resistance. Protodioscin is a phytochemical agent derived from *Tribulus terrestris* plant, which has been clinically proven to improve sexual desire and enhance erection via the conversion to DHEA (De-Hydro-Epi-Androsterone) (Adimoelja A. Phytochemicals and the breakthrough of traditional herbs in the management of sexual dysfunctions. Int J Androl. 2000; 23:82-4). Protodioscin has a pro-erectile activity. The enhanced relaxant effect observed is probably due to increase in the release of nitric oxide from the endothelium and nitrergic nerve endings, which may account for its claims as an aphrodisiac (Adaikan P G, Gauthaman K, Prasad R N. Pro-erectile pharmacological effects of *Tribulus terrestris* extract on the rabbit corpus cavernosum. Ann Acad Med Singapore. 2000; 29:22-6). Improvement in sexual behavior parameters observed in rats could be secondary to the androgen increasing property of *Tribulus Terrestris* (Protodioscine) that was observed in earlier study on primates. The increase in intracavernous pressure which confirms the proerectile aphrodisiac property of *Tribulus Terrestris* could possibly be the result of an increase in androgen and subsequent release of nitric oxide from the nerve endings innervating the corpus cavernosum (Gauthaman K, Ganesan A P, Prasad R N. Sexual effects of puncturevine (*Tribulus terrestris*) extract (protodioscin): an evaluation using a rat model. J Altern Complement Med. 2003; 9:257-65). *Tribulus terrestris* (TT) has long been used in the traditional Chinese and Indian systems of medicine to improve sexual functions in man. Treatment of castrated rats with *Tribulus Terrestris* extract showed increase in intracavernous pressure that was statistically significant. There was also a mild to moderate improvement of the sexual behavior parameters as evidenced by increase in mount and intromission frequencies; decrease in mount, intromission and ejaculation latencies, as well as post-ejaculatory interval. These results were statistically significant. It is concluded that *Tribulus* extract appears to possess aphrodisiac activity probably due to androgen increasing property of *Tribulus*—observed in earlier study on primates—(Gauthaman K, Adaikan P G, Prasad R N. Aphrodisiac properties of *Tribulus Terrestris* extract (Protodioscin) in normal and castrated rats. Life Sci. 2002; 71:1385-96). *Tribulus* contains no less than 46 active principles.

Organizational Improvers.

*Ginkgo biloba* (Ginkgo) Contains ginkgolides, bilobalides, bioflavones and flavone glycosides. Flavone glycosides include quercetin, 3-methylquercetin and kaempferol. Quercetin, myrcetin and the rest of the flavonoid fraction of the extract have antioxidant and free radical scavenger effects. Flavonoids increase blood flow. Their antioxidant properties and membrane stabilizing activity increase the tolerance to hypoxia. They improve cellular metabolism and protect against damage caused by ischemia. Ginkgolide B is a powerful PAF inhibitor, which bonds to membrane receptors and is an antagonist of platelet aggregation. It also has anti-inflammatory properties by reducing vascular permeability and has vasodilator effects by inhibiting the liberation of thromboxane A2 and prostaglandins. Ginkgo's flavonoids have antioxidant properties because they capture free radicals and prevent lipid peroxidation related to endothelial damage. Improve cellular metabolism and protect tissues against damage produced by ischemia. In an open trial *Ginkgo biloba* was found to be 84% effective in treating antidepressant-induced sexual dysfunction predominately caused by selective serotonin reuptake inhibitors. Women were more responsive to the sexually enhancing effects of *Ginkgo biloba* than men, with relative success rates of 91% versus 76%. *Ginkgo biloba* generally had a positive effect on all 4 phases of the sexual response cycle: desire, excitement (erection and lubrication), orgasm, and resolution—afterglow—(Cohen A J, Bartlik B. *Ginkgo biloba* for antidepressant-induced sexual dysfunction. J Sex Marital Ther. 1998; 24:139-43). In a triple-blind, randomized, placebo-controlled, clinical trial of *Ginkgo biloba* given to 24 patients with sexual impairment due to antidepressant drugs, there were some spectacular individual responses in both groups (Wheatley D. Triple-blind, placebo-controlled trial of *Ginkgo biloba* in sexual dysfunction due to antidepressant drugs. Hum Psychopharmacol. 2004; 19:545-8). Also, the sub fractions of *Ginkgo biloba* have a relaxing effect on corpus cavernosum tissue (Paick J S, Lee J H. An experimental study of the effect of *ginkgo biloba* extract on the human and rabbit corpus cavernosum tissue. J Urol. 1996; 156:1876-80). Ginkgo provides at least 59 active principles in a single therapeutic.

Herba epimedii (*Epimedium sagittatum, E. brevicornu, E. acuminatum, E. koreanum, E. pubescens, E. leptorrhizum* and *E. wushanense*.) *Epimedium sagittatum*: Epimedii is a very powerful tonic herb. Its name can be translated as "the herb for the man who likes sex too much, like a goat". This is what Epimedii is famous for. Women, too, take this herb to increase their sexual drive. This herb has been studied extensively in laboratories and clinics in modern China, Korea and Japan. It stimulates the sensory nerves throughout the body, and in particular the genital region. Epimedii increases sperm production in men; also, shown to have a moderate androgen-like influence on the testes, prostate gland and anal muscles, which will influence sexual desire and activity (Teeguarden, R. The Ancient Wisdom of the Chinese Tonic. Warner Books, 1999; 162-4). Its main Active principles are: flavonoids, prenylflavones, flavones and flavonol glycosides: Prenylflavones: yinyanghuo A, B, C, D, and E. Flavonoids: chryso-eriol, quercetin, apigenin, apigenin 7,4'-dimethyl ether, kaempferol, kaempferol-3,7-O-alpha-L-dirhamnoside, luteolin, tricin, icaritin, icariside 1,2-(p-hydroxyphenoxy)-5, 7-dihydroxy-6-prenylchromone, Magnoflorine, sagittatoside A and B, hyperoside, hyperin. Flavonol glycosides: Icariin; anhydroicaritins (korepimedoside A and korepimedoside B, epimedokoreanoside-I, caohuoside-B) and desmethylanhydroicaritin; baohuosides II, III, V, VI; epimedoside A and E, diphylloside A and B, epimedin B and C, ikarisosides A, B, C and F, wanepimedoside A. Flavones: wushanicariin; hexandraside E; icarisid I and II. Icariin isolated from *Epimedium* is considered to be the major pharmacological active component of Herba Epimedii. *Epimedium* has been reputed to have sexual stimulation effects on males. Extract of *Epimedium* relax the corpus cavernosum smooth muscle through multi-targets in on nitric oxide (NO)/cyclic guanosine monophosphate/PDE 5 pathway and might bring into perspective the treatment strategy for those patients with erectile dysfunction. (Chiu J H, Chen K K, Chien T M. *Epimedium brevicornum* Maxim extract relaxes rabbit corpus cavernosum through multitargets on nitric oxide/cyclic guanosine monophosphate signaling pathway. Int J Impot Res. 2006: January). The traditional idea that Herba Epimedii warms the kidney and thus invigorates "Yang" has been tested and verified by modern pharmacological methods. Experimental findings indicate that well processed Herba Epimedii helps improve the sexual function (Niu R. Action of the drug Herba Epimedii on testosterone of the mouse plasma and its accessory sexual organ before and after processing. Zhongguo Zhong Yao Za Zhi. 1989; 14:530-2, 574).

*Serenoa repens* (Saw palmetto, Sabal serrulata, Scrub-Palmetto). Its main active principles are saturated fatty acids: lauric, myristic, palmitic, capric, caprylic; and unsaturated fatty acids: oleic, linoleic and linolenic. These fatty acids have demonstrated inhibiting action on 5-Alpha-Reductase, enzyme which transforms Testosterone into Dihydrotestosterone (Habib F K, Ross M, Ho C K. *Serenoa repens* (Permixon) inhibits the 5alpha-reductase activity of human prostate cancer cell lines without interfering with PSA expression. Int J Cancer. 2005; 114:190-4) (Raynaud J P, Cousse H, Martin P M. Inhibition of type 1 and type 2 5alpha-reductase activity by free fatty acids, active ingredients of Permixon. J Steroid Biochem Mol Biol. 2002; 82:233-9). The lipidosterolic extract of *Serenoa repens* significantly improved sexual function during the second year treatment in BPH symptomatic patients (Pytel Y A, Vinarov A, Lopatkin N. Long-term clinical and biologic effects of the lipidosterolic extract of *Serenoa repens* in patients with symptomatic benign prostatic hyperplasia. Adv Ther. 2002; 19:297-306). *Serenoa* contains at least 13 active principles.

Vitamin E In a randomized and open clinical trial, vitamin E and selenium supplementation produced a significant improvement of sperm motility. The results confirmed the protective and beneficial effects of vitamin E and selenium on semen quality and advocate their use in male infertility treatment (Keskes-Ammar L, Feki-Chakroun N, Rebai T. Sperm oxidative stress and the effect of an oral vitamin E and selenium supplement on semen quality in infertile men. Arch Androl. 2003; 49:83-94). Vitamin E protects against ROS mediated damage on spermatozoa (Verma A, Kanwar K C. Effect of vitamin E on human sperm motility and lipid peroxidation in vitro. Asian J Androl. 1999; 1:151-4). The decrease in reduced glutathione—an endogenous antioxidant—levels in azoospermic and oligozoospermic conditions may cause disruption in the membrane integrity of spermatozoa as a consequence of increased oxidative stress (Bhardwaj A, Verma A, Majumdar S. Status of vitamin E and reduced glutathione in semen of oligozoospermic and azoospermic patients. Asian J Androl. 2000; 2:225-8). In a Clinical, Randomized Controlled Trial, treatment of asthenospermic patients with oral Vitamin E significantly decreased the MDA concentration in spermatozoa and improved sperm motility. Eleven out of the 52 treated patients (21%) impregnated their spouses; nine of the spouses successfully ended with normal term deliveries, whereas the other two aborted in the first trimester. No pregnancies were reported in the spouses of the placebo-treated patients (Suleiman S A, Ali M E, Zaki Z M. Lipid peroxidation and human sperm motility: protective role of vitamin E. J Androl. 1996; 17:530-7). Oligoasthenoteratozoospermic men were supplemented for a period of 6 mo with Se and Vit E. Statistically significant increases were observed for sperm motility, percent live, and percent normal spermatozoa. These improvements are likely to be "supplementation-dependent," since all of the parameters returned to baseline values during the post-treatment period (Vezina D, Mauffette F, Roberts K D. Selenium-vitamin E supplementation in infertile men. Effects on semen parameters and micronutrient levels and distribution. Biol Trace Elem Res. 1996; 53:65-83).

Example 2

Composition—Erectile Dysfunction

A particularly preferred composition is shown in Table 1. Ratios reflect the concentration of active ingredient over the natural state, and the amounts provided are mg of extract. Obviously, the amount should be increased where the strength is reduced, and vice versa. A particularly preferred composition is shown in Table 1.

TABLE 1

| Composition | | |
|---|---|---|
| Active Agent | Ratio | Amount (mg) |
| Energy enhancers | | |
| *Ajuga turkestanica* | 5:1 | 74 |
| *Aralia mandshurica* | 5:1 | 74 |
| *Eleutherococcus senticosus* | 5:1 | 74 |
| *Lepidium meyenii* | 10:1 | 61 |
| *Panax ginseng* | 5:1 | 14 |
| *Pfaffia paniculata* | 5:1 | 49 |
| *Ptychopetalum olacoides* | 10:1 | 74 |
| *Rhaponticum carthamoides* | 6:1 | 16 |
| Bio-Intelligence modulators | | |
| *Astragalus membranaceus* | 5:1 | 74 |
| *Elettaria cardamomum* | 5:1 | 74 |
| *Tribulus terrestris* | 5:1 | 98 |
| Organization improvers | | |
| *Ginkgo bilova* | 50:1 | 25 |
| *Herba epimedii* | 5:1 | 74 |
| *Serenoa repens* | 5:1 | 25 |
| Vitamin E | 1:1 | 12 |
| Total | | 902 |

Example 3

Erectile Dysfunction Disorder

The effectiveness of the erectile dysfunction synergistic composition, formulated under the Systemic Medicine principles, was evaluated thought a retrospective, multicenter, descriptive two year study of 72 patients with erectile dysfunction. The composition improved erectile dysfunction in 90.3% of the patients; also, there was a marked improvement in Quality of Life. No side or secondary effects were observed in 98.6% of the study group. However, the effects observed did not warrant the suspension of the treatment. The erectile dysfunction formulation demonstrated to be an extraordinary treatment for patients with erectile dysfunction, reason why it should be considered as a treatment.

Example 4

Principles for Selecting Synergistic Combinations

In order to explain the formulation encompassed by the invention, beneficial plants and nutraceuticals have been categorized into one of three groups, each of which should be present for synergistic effect. The classifications are: Energy, Bio-Intelligence and Organization. Plants and nutraceuticals classified under Energy are associated with ATP synthesis (such as the Krebs cycle, oxidative phosphorylation, beta-oxidation, etc.). Plants and nutraceuticals classified under Bio-Intelligence are those that regulate the neuroendocrine and immunological systems and cellular processes, thus controlling the interactions between the various systems in the body. Finally, plants and nutraceuticals classified under Organization are those that relate to the structure and function of specific organs. Combinations of plants and nutraceuticals from these three classification groups have synergistic effect because they address each necessary component of cellular and organic health—in effect they provide the triangle on which healing is fully supported. This is illustrated in FIG. 1.

An illustrative example of synergy in medicinal plants is an in vitro study that demonstrates how the activity of herbal Berberine alkaloids is strongly potentiated by the action of 5'-methoxyhydnocarpin (5'-MHC)—an active principle of another phytomedicine (denominated Hydnocarpus wightiana).

It shows a strong increase of accumulation of berberine in the cells in the presence of 5'-MHC, indicating that this plant compound effectively disabled the bacterial resistance mechanism against the berberine antimicrobial, thus showing the synergy of both substances. Stermitz F R, et al., Synergy in a medicinal plant: antimicrobial action of berberine potentiated by 5'-methoxyhydnocarpin, a multidrug pump inhibitor. Proc Natl Acad Sci USA. 2000; 97:1433-7.

A further demonstration may be provided of synergistic effect on a molecular scale by studying the gene expression profile changes in response to various plant ingredients and combinations thereof. Experiments are already underway demonstrating the expression profile in response to the formulations. We will be aided in this work because researchers have already begun studying the expression profiles of various medicinal plants, thus providing a database of knowledge from which to build. E.g., Gohil, et al., mRNA Expression Profile of a Human Cancer Cell Line in Response to *Ginkgo Biloba* Extract: Induction of Antioxidant Response and the Golgi System, Free Radic Res. 2001; 33:831-849.

Finally there may be further presentation of gene expression results using whole-genome microarray analysis to demonstrate the formulation's capability to provide gene activation (upregulation or downregulation).

What is claimed is:

1. A phytoceutical composition, comprising 74 mg of *Ajuga turkestanica,* 74 mg of *Aralia mandschurica,* 74 mg of *Eleutherococcus senticosus,* 61 mg *Lepidium meyenii,* 14 mg of *Panax ginseng,* 49 mg of *Pfaffia paniculata,* 74 mg of *Ptychopetalum olacoides,* 16 mg of *Rhaponticum carthamoides,* 74 mg of *Astragalus membranaceus,* 74 mg of *Elettaria cardamomum,* 98 mg of *Tribulus terrestris,* 25 mg of *Ginkgo biloba,* 74 mg of *Herba epimedii,* 25 mg of *Serenoa repens* and 12 mg of Vitamin E together with pharmaceutically acceptable excipients.

2. A method of treating erectile dysfunction comprising administering an effective amount of the composition of claim 1 to a patient to alleviate said disease.

* * * * *